United States Patent [19]

Speranza et al.

[11] Patent Number: 4,847,380

[45] Date of Patent: Jul. 11, 1989

[54] HIGH MOLECULAR WEIGHT POLYALKOXYAMIDE, UREA OR URETHANE-CONTAINING PIPERIDINE RADICAL

[75] Inventors: George P. Speranza, Austin; Jiang-Jen Lin, Round Rock, both of Tex.

[73] Assignee: Texaco Inc., White Plains, N.Y.

[21] Appl. No.: 78,313

[22] Filed: Jul. 27, 1987

[51] Int. Cl.$^4$ .................... C07D 401/12; C08K 5/54
[52] U.S. Cl. ..................................... 546/190; 524/103
[58] Field of Search ........................................ 546/190

[56] References Cited

U.S. PATENT DOCUMENTS 4,725,634  2/1988  Ishii et al. ........................... 546/190

Primary Examiner—Robert T. Bond
Attorney, Agent, or Firm—Jack H. Park; Kenneth R. Priem; Cynthia L. Kendrick

[57] ABSTRACT

Novel high molecular weight polyalkoxyamine derivatives are prepared which contain a polyalkoxyamide, urea or urethane backbone with a piperidine terminal radical.

The structures can be represented by the following three classes of compounds:

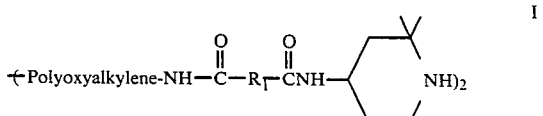

Amide Linkage

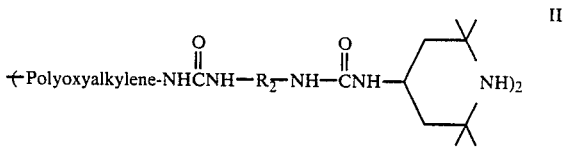

Urea Linkage

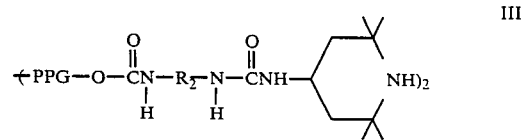

Urethane Linkage where $R_1$ is from dibasic acid, e.g. adipic or dimer acid; $R_2$ is from diisocyanate, e.g. IPDI or TMXDI.

4 Claims, No Drawings

HIGH MOLECULAR WEIGHT POLYALKOXYAMIDE, UREA OR URETHANE-CONTAINING PIPERIDINE RADICAL

FIELD OF THE INVENTION

The present invention relates to new polyoxyalkyleneamine derivatives. More particularly, this invention relates to novel high molecular weight polyoxyalkyleneamido amide, polyoxyalkylene polyurea, polyoxyalkylene polyurea urethane backbones containing a piperidine radical. Still more particularly, this invention relates to novel molecules containing a high molecular weight polyalkoxyamide, urea or urethane backbone with a piperidine such as 2,2,6,6-tetramethylpiperidine as the terminal radical, prepared in two steps by reacting a polyoxyalkylene diamine or a polyoxyalkylene glycol with a dicarboxylic acid or a diisocyanate and subsequently reacting the intermediate with a tetralkyl piperidine at a range of temperatures depending on the reactants and the desired products.

These novel compounds are especially useful as light stabilizers for synthetic polymers.

BACKGROUND OF THE INVENTION

It is known that synthetic polymers undergo a progressive change in their physical properties, such as loss of their mechanical strength and color changes, when they are exposed to sunlight or other sources of ultraviolet light.

It is hitherto well known that synthetic resins such as polyethylene, polypropylene, polyvinyl chloride, polyurethane, ABS resin, etc. deteriorate by the action of light, thereby showing a remarkable reduction in physical properties followed by phenomena such as softening, brittleness, discoloration and the like.

For the purpose of preventing such deterioration by light, the use of various photostabilizers is conventional. Such photostabilizers include for example 2-hydroxy-4-methoxybenzophenone. 2-hydroxy-4-n-octoxybenzophenone, 2-(2-hydroxy-5-methylphenyl)benzotriazole, 2-(2-hydroxy-3-tert-butyl-5-methylphenyl)-5-chlorobenzotriazole, 2-(2-hydroxy-3,5-dipentylphenyl)benzotriazole, ethyl 2-cyano-3,3-diphenylacrylate, 2,4-di-tert-butylphenyl 3,5-di-tert-butyl-4-hydroxybenzoate. [2,2'-thiobis(4-tert-octylphenolate)in-butylamine nickel(II), Ni salt of bis(3,5-di-tert-butyl-4-hydroxybenzylphosphoric acid)monoethyl ester, bis(2,2,6,6-tetramethyl-4-piperidyl)sebacate and the like. These photostabilizers, however, are not yet quite satisfactory in terms of light fastness, when used alone or in combination of sulfur-containing antioxidants(s).

U.S. Pat. No. 4,578,472 discloses a 2,2,6,6-tetramethylpiperidine derivative used for prevention of deterioration by light of synthetic resins produced by reacting a 4-amino-2,2,6,6-tetramethylpiperidine compound represented by the formula:

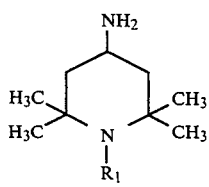

wherein $R_1$ represents a hydrogen atom or methyl group with a halogenated carboxylic acid or ester represented by the formula:

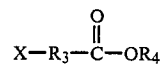

wherein X represents a halogen atom, $R_3$ represents an alkylene group having one to four carbon atoms, and $R_4$ represents a hydrogen atom or lower alkyl group and then reacting the resulting reaction product with a 4-hydroxy-2,2,6,6-tetramethylpiperidine compound represented by the formula:

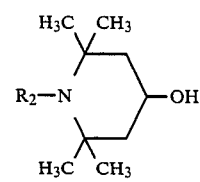

wherein $R_2$ represents a hydrogen atom or methyl group, in the presence of a basic catalyst.

In studying the destructive action of sunlight, it is clear that the rate of such degradation is greater, the greater the specific surface area of the polymer; therefore, manufactured articles with extensive surface development, such as fibers, tapes and films, more readily suffer photo-oxidative degradation. In order to delay the negative effect of ultraviolet radiation on synthetic polymers, it has been proposed to use various stabilizers which protect against light; in particular, for the light stabilization of articles of small thickness, such as fibers, tapes and films, it has been proposed to use products of polymeric nature, which contain polyalkylpiperidine radicals which, because of their relatively high molecular weight, are markedly resistant to volatilization and to extraction by water. Some of these products also show a marked effecacy as light stabilizers; in particular, U.S. Pat. No. 4,086,204 has claimed polytriazine compounds comprising, for example, compound of the formula

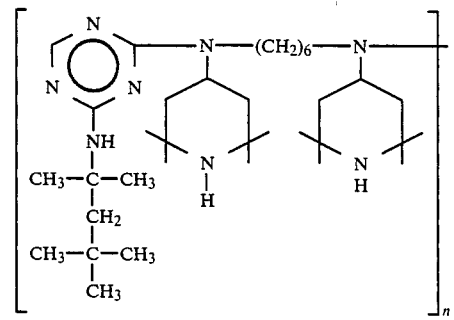

U.S. Pat. No. 4,102,248 has claimed, as stabilizers for polyolefins, polyamines comprising, for example, the compound of the formula:

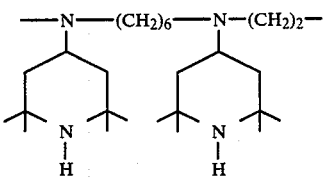

and U.S. Pat. No. 4,232,131 has claimed, likewise as stabilizers for polymers, polyamides comprising, for example, the compound of the formula:

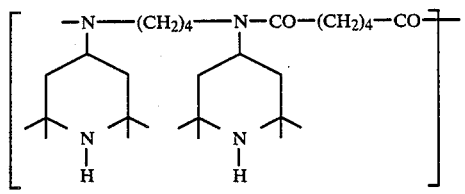

The results obtained with the above-mentioned products were, however, not entirely satisfactory, so that a further improvement was desirable.

In U.S. Pat. No. 4,526,972, U.V. Stabilizers are described containing polyoxyalkylene derivatives of tetramethyl piperadines

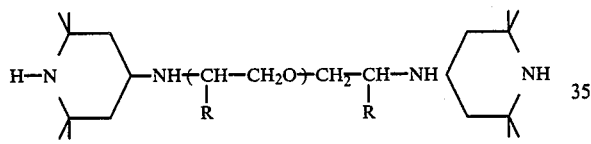

In this work R is H or $CH_3$.

The invention of U.S. Pat. No. 4,578,454 relates to novel products of a polymeric nature, which contain piperidine radicals and have shown a surprising and unforeseeably higher activity as light stabilizers for synthetic polymers, as compared with products of the state of the art. The activity of the novel stabilizers is of particular interest for polyolefin films, fibres and tapes.

That invention relates particularly to polyaminoamides of the general formula (I):

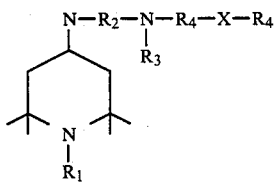

in which $R_1$ is hydrogen, O., $CH_2CN$, $C_1$–$C_{12}$-alkyl, $C_3$–$C_{12}$-alkenyl or -alkynyl, substituted or unsubstituted $C_7$–$C_{12}$-aralkyl or $C_1$–$C_{12}$-acyl, $R_2$ is $C_2$–$C_{18}$-alkylene, $C_5$–$C_{18}$-cycloalkylene, $C_6$–$C_{18}$-arylene or $C_7$–$C_{18}$-aralkylene, $R_3$ is hydrogen, $C_1$–$C_{18}$-alkyl, $C_5$–$C_{18}$-cycloalkyl, substituted or unsubstituted $C_6$–$C_{18}$-aryl, substituted or unsubstituted $C_7$–$C_{18}$-aralkyl or a radical of the formula (II).

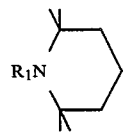

in which $R_1$ is as defined above, the $R_4$'s are

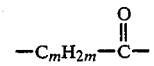

radicals with the carbonyl group attached either to X or to N and in which m is an integer from 1 to 12, X is a divalent radical containing 1 or more hetercyclic radicals of the formula (III), (IV) or (V).

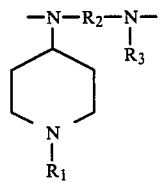

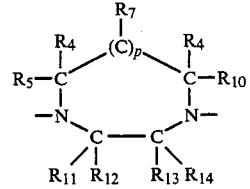

in which $R_1$, $R_2$ and $R_3$ are as defined above, p is zero or 1, $R_5$, $R_6$, $R_7$, $R_8$, $R_9$, $R_{10}$, $R_{11}$, $R_{12}$, $R_{13}$ and $R_{14}$ are hydrogen or methyl, $R_{15}$ is hydrogen. $C_1$–$C_{18}$ alkyl, $C_5$–$C_{18}$ cycloalkyl, substituted or unsubstituted $C_6$–$C_{18}$ aryl, substituted or unsubstituted $C_7$–$C_{18}$ aralkyl or a radical of the formula (II), and n is an integer from 2 to 100.

A good review of this subject is found in "Polymer Stabilization and Degradation", P. P. Klemchuk, Editor, American Chemical Society, Washington, D.C. 1985, Chapters 1–4, 11.

In the instant invention there has been devised a method for preparing a piperidine derivative having a structure containing a polyalkoxylamide, urea or urethane backbone. This novel structure allows certain advantages over the art. The advantages include.

1. Simple preparation methods.
2. Low cost products from readily available starting materials.
3. Products which can be either water-soluble or water-insoluble.
4. Products with a low volatility which are difficult to remove from the polymers they are protecting.

SUMMARY OF THE INVENTION

In accordance with the present invention, light stabilizing problems with polymers such as those mentioned above are significantly reduced through the provision of a polyalkoxyamide, urea, or urethane backbone containing a piperidine as the terminal radical.

The light stabilizing products are the product of a two-step reaction between a diamine or polypropylene glycol and a dicarboxylic acid or a diisocyanate followed by reaction with a piperidine.

The structures can be represented by the following three classes of compounds:

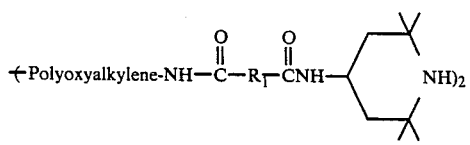

Amide Linkage

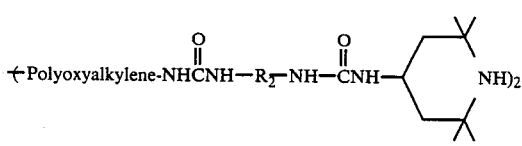

Urea Linkage

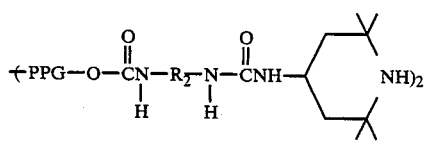

Urethane Linkage where $R_1$ is from dibasic acid, e.g. adipic or dimer acid; $R_2$ is from diisocyanate, e.g. isophorone diisocyanate, tetramethylxyxlene/diisocyanate.

DETAILED DESCRIPTION OF THE INVENTION

The novel polyalkyoxyamide, polyalkoxyurea or polyalkoxyurethane with piperidine radicals represented by the structures above can be synthesized in two steps by reacting a polyoxyalkylene diamine of the formula:

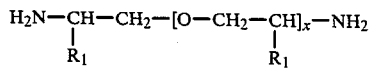

or a polypropylene glycol of the formula:

with a dibasic acid or a diisocyanate and subsequently reacting it with a tetramethylpiperidine.

The temperature for the first step of the reaction is from about 150° to 250° C. and for the second step from about 150° C. to 250° C. when dicarboxylic acids are used. When diisocyanates are used the temperatures may be from below ambient temperatures to about 120° C.

The Polyoxyalkylenediamine

The polyoxyalkylene polyamine starting materials for the present invention include polyoxypropylenediamines, polyoxyethylenediamines and polyoxyalkylenediamines containing mixtures of both ethylene oxide and propylene oxide and, preferably, mixtures of from about 5 to about 40 wt % of ethylene oxide with, correspondingly, from about 95 to 60 wt % of propylene oxide. Where mixed propylene oxide/ethylene oxide polyols are employed, the ethylene oxide and propylene oxide may be premixed prior to reaction to form a hetero copolymer, or the ethylene oxide and the propylene oxide may be sequentially added to the ethoxylation kettle to form block oxypropylene/oxyethylene copolymers.

In general, the polyoxyalkylene polyamine starting material may be defined as a polyoxyalkylene polyamine having the formula:

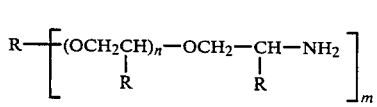

wherein R is the nucleus of an oxyalkylation-susceptible polyhydric alcohol containing 2 to 12 carbon atoms and 2 and 3 hydroxyl groups, and R' is hydrogen or methyl, n is a number having an average value of 0 to 50, and m is an integer having a value of 2 to 3.

In general, the average molecular weight of the polyoxypropylene diamine starting material will be from about 200 to about 5000.

One group of appropriate polyoxyalkylene diamines that may be used are those that are sold by the Texaco Chemical Co. as JEFFAMINE® D-series products having the formula:

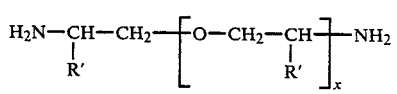

wherein R' independently represents hydrogen or methyl and x is a number having an average value of about 1 to about 60.

Representative products having this structural formula include polyoxypropylene diamines having an average molecular weight of about 400 wherein x has a value between about 5 and 6 (JEFFAMINE® D-400 amine), and a polyoxypropylene diol product having an average molecular weight of about 2000 wherein x has a value of about 33 (JEFFAMINE® D-2000 amine).

The polyols used can be polyoxypropylene glycols, polyoxyethylene glycols or mixed polyoxyethylene propylene glycols of molecular weight of about 200 to 2000, having the formula:

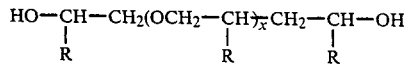

where X has a value of about 2 to 33 and R is hydrogen or methyl.

Polyols which work well and which are employed in the examples comprise polypropylene glycols having the formula:

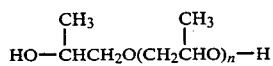

wherein the molecular weight is from 200 to 2000. One commercially available group of polyproplene glycols are JEFFOX® PPG products produced by Texaco Chemical Co.

When the high molecular weight polyol is DPG-2000, the two-step reaction product can be represented as follows:

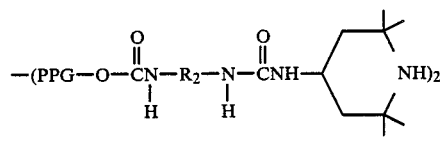

The Dibasic Acid or Diisocyanate

The dibasic acids used in the reaction comprise $C_2$ to $C_{36}$ dicarboxylic acids. Examples of useful dibasic acids include oxalic, glutaric, sebacic, isophthalic, terephthalic, azelaic, adipic or dimer acid.

The isocyanate component for the present invention may be any suitable isocyanate having the desired functionality and is preferably organic diisocyanates. The aliphatic diisocyanates are preferred. Although diisocyanates are referred to with preference, other higher polyisocyanates can be used in combination with diisocyanates and/or monoisocyanates. Examples of suitable aliphatic diisocyanates are aliphatic diisocyanates such as 1,4-tetramethylene diisocyanate, trimethylhexane diisocyanate, 1,6-hexamethylene diisocyanate, 1,4-cyclohexyl diisocyanate, isophorone diisocyanate, xylylene diisocyanate, m - and p- tetramethylxylylene diisocyanate, 4,4′methylene-bis(cyclohexyl isocyanate), 2,2,4-trimethylhexamethylene diisocyanate, 2,4,4-trimethylhexamethylene diisocyanate and mixtures thereof. Substituted organic polyisocyanates can also be used in which the substituents are nitro, chloro, alkoxy and other groups which are not reactive with active hydrogens and provided the substituents are not positioned to reach the isocyanate group unreactive or adversely affect the intended use of the diamine.

Preferred alkylisocyanates for producing amines containing urea groups include isophorone diisocyanate and tetramethylxylene diisocyanate.

The Piperidine

In the second step of the reaction the intermediate product of the reaction of a diamine or polyol and a dibasic acid or diisocyanate is reacted with a piperidine which provides the terminal radical for the product.

The piperidine compound is generally one represented by the following formula:

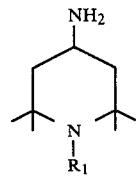

wherein $R_1$ represents hydrogen, alkyl group or an oxy group.

Suitable piperidines include tetraalkylpiperidine. A piperidine used with good results was 2,2,6,6-tetramethylpiperidine.

Preparation of the Novel Derivatives

It is been discovered in accordance with the present invention that a novel high molecular weight compound containing a polyalkoxyamide, urea or urethane backbone with a piperidine terminal radical is formed when a polyoxyalkyldiamine or a polyol is reacted with a dibasic acid or an isocyanate and then reacted with a 2,2,6,6-tetramethylpiperidine.

Where a diamine is reacted with a dicarboxylic acid the reaction temperature is from about 150° C. to 250° C. and preferably about 200° C. This is followed by the reaction with tetramethylpiperidine which takes place at a temperature of from about 150° C. to 250° C. and preferably about 180° C.

Where a diamine is reacted with a diisocyanate the effective temperature is lower, for example, from 0° to 60° and preferably around 15° C. It is noteworthy that colorless products are obtained under these conditions.

The temperature can range from 50° to 150° C. and is preferably about 80°-100° C. in the case where a polyol is reacted with a diisocyanate. Here a tin catalyst is desirable to speed the reaction. Generally, the tin catalyst should be an organo tin compound. Tin compounds which work include dibutyltin dilaurate, dioctyltin dilaurate, etc.

The first step of the reaction is complete when essentially all the isocyanates or dibasic acids have reacted with the primary amine groups of the polyoxyalkylene diamine.

The second step is complete when the intermediate dibasic acids or diisocyanates react with the tetraalkylpiperidine.

The novel structures that are formed by the process of the invention are colorless, or light colored viscous liquids or semisolids having a molecular weight within the range of about 500 to about 4000.

A variety of molecular configurations are possible for the compounds of the present invention, depending on the starting materials. The structures are described by the following three classes of compounds:

Amide Linkage

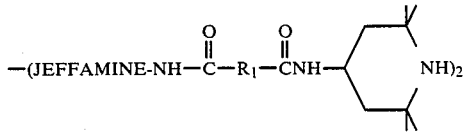

Urea Linkage

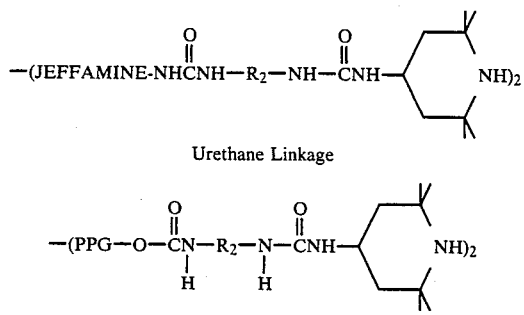

where $R_1$ is from dibasic acid, e.g. adipic or dimer acid and $R_2$ is from diisocyanate, e.g. IPDI or TMXDI.

Piperidine derivatives have been used previously as light stabilizers, but the improvements of this system over similar work in the art include the following:
1. Simple preparation methods.
2. Colorless to lightly colored products.
3. Water-soluble and water-insoluble products.
4. Low cost raw materials.
5. Liquid or low melting solids products for case of handling.

The following examples are given in order to illustrate the invention and are not intended to limit the scope of the invention.

EXAMPLE 1

D-2000-Dimer Acid Adduct

To a 2-liter 3-necked flask equipped with a thermometer, mechanical stirrer, Dean-Stark trap and nitrogen inlet line, was charged JEFFAMINE ® D-2000 amine (800 g) and dimer acid (Emery's Empol 1010, made by dimerizing $C_{18}$ unsaturated acids, primarily oleic and linoleic acids) (422 g). The mixture was heated to 200°–222° C. for three hours to remove water (ca. 11 ml). The viscous product was analyzed to be 0.69 meq/g for acidity and 0.01 meq/g for amine content. The average molecular weight was estimated to be about 2900.

EXAMPLE 2

D-2000-Dimer Acid-TMAP

To a 500 ml 3-necked flask equipped with a thermometer, stirrer, Dean-Stark trap and nitrogen line was charged D-2000-Dimer acid adduct (6199-4, 200 g, ca. 0.07 mole) and 2,2,6,6-tetramethyl-4-amino-piperidine (TMAP, 21.5g, ca. 0.14 M). The mixture was gently heated to 180° C. for ca. 4 hours. Water, 3.1 ml, was removed. The resulting product was a transparent, pourable, yellow liquid, having an analysis of 0.56 meq/g for total amine and 0.49 meq/g for secondary amine.

EXAMPLE 3

JEFFAMINE ® D-400 Amine-Adipic Acid-TMAP

Following the procedures described above, the adduct of D-400-adipic acid-TMAP (1:2:2) was obtained from 200 g of D-400-adipic acid adduct and 102 g of TMAP under conditions of 175°–180° C. for about 4 hours. The analysis indicated 2.37 meq/g for total amine (calc. 2.26) and 2.10 meq/g for secondary amine. The product was light brown, transparent semisolid.

EXAMPLE 4

JEFFAMINE ® ED-2001 Amine-Adipic Acid-TMAP

Following the similar procedures described above, the mixture of ED-2001-adipic acid adduct (215 g, 0.1 M) and TMAP 31.2 g, 0.2 M) was heated to 182°–192° C. for about 3 hours. The product mixture was light grey solid (mp ca. 35° C.), and water soluble. The analysis indicated 0.90 meq/g for total amine and 0.77 meq/g for secondary amine (calc. 0.82).

EXAMPLE 5

JEFFAMINE ® D-2000 Amine-IPDI-TMAP

To a 1-liter 3-necked flask equipped with thermometer, stirrer, dropping funnel and nitrogen inlet was, charged isophorone diisocyanate (44.4 g, 0.2 M). The diisocyanate was cooled to 12° C. and a mixture of JEFFAMINE ®D-2000 amine (200g, 0.1M) and isopropanol (200 g) was added dropwise over a period of about 2 hours. This isocyanate precursor was transferred into an addition funnel, then added to the stirring mixture of TMAP (31.2 g, 0.2 M) and i-PrOH (60 g) at 18° C. over a 30 minute period of time. The final solution was subjected to reduced pressure (~40 mm) the solvent was removed at about 130° C. The resulting product was a nearly colorless, transparent semisolid. Analysis gave 0.75 meq/g for total amine and 0.73 meq/g for secondary amine (calc. 0.73 meq/g).

EXAMPLE 6

JEFFAMINE ® D-2000 Amine-TMXDI-TMAP

Following the experimental procedures described above, the product of D-2000-TMXDI-TMAP from the reaction of (1) tetramethylxylene diisocyanate (American Cyanamide, 48.8 g, 0.2 M), (2) JEFFAMINE ® D-2000 amine (200 g, 0.1 M) and i-PrOH (200 g) and (3) TMAP (31.2 g, 0.2 M) and i-PrOH (60 g). The final product was light yellow solid with analysis of 0.75 meq/g for total amine, 0.10 meq/g for primary amine, (calc. 0.72 meq/g for total amine).

EXAMPLE 7

PPG-2000-IPDI-TMAP

To a 500 ml 3-necked flask equipped with thermometer, dropping funnel, stirrer and nitrogen inlet was, charged PPG-2000 (200 g, 0.1 M), T-13 (dibutyl tin dilaurate 0.3 g) and isophorone diisocyanate (44.4 g, 0.2 M). The mixture was heated to 80°–85° C. for two hours, then cooled to 10° C. at this temperature, TMAP (31.2 g, 0.2 M) was added in one portion. The resulting material was light yellowish semisolid. The analysis showed 0.79 meq/g for total amine content (calc. 0.73) and 0.06 meq/g for primary amine.

What is claimed is:
1. A 2,2,6,6,-tetramethylpiperidine represented by the formula:

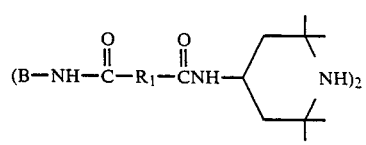

wherein $R_1$ represents the reaction product residue of a dicarboxylic acid from the group consisting of oxalic, glutaric, sebacic, isophthalic, terephthalic, azaleic, adipic and dimer acid and wherein B represents 3 to 34 linkages of a polyoxyalkylene amine from the group consisting of polyoxproplenediamines, polyoxyethylenediamines and mixed poly(oxyethylene/oxypropylene)diamines.

2. A 2,2,6,6,-tetramethylpiperidine represented by the formula:

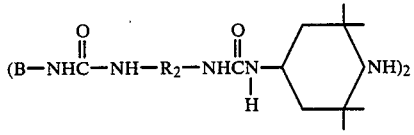

wherein $R_2$ represents the reaction product residue of an aliphatic diisocyanate having 6 to 36 carbons and B represents 3 to 34 linkages of a polyoxyalkylene amine from the group consisting of polyoxpropylenediamines, polyoxethylenediamines and mixed poly(oxyethlene/oxpropylene)diamines.

3. A 2,2,6,6,-tetramethylpiperidine represented by the formula:

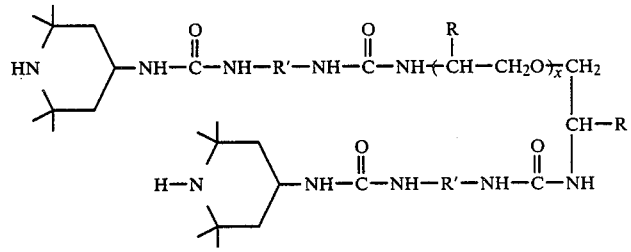

wherein $R_2$ represents the reaction product residue of an aliphatic diisocyanate having 6 to 36 carbons and G represents a polyol from the group consisting of polyoxypropylene glycols, polyoxyethylene glycols or mixed poly(oxyethylene/oxypropylene) glycols of a molecular weight from about 200 to 2000.

4. A compound of the formula:

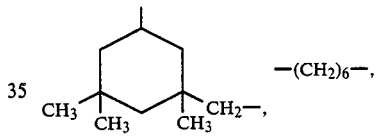

where R=hydrogen or methyl and x=2 to 34, and R' is $-(CH_2)_6-$,

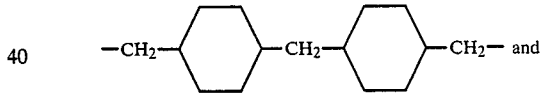

$-CH_2-$⌬$-CH_2-$⌬$-CH_2-$ and

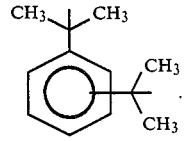

* * * * *